United States Patent [19]

Friedman et al.

[11] Patent Number: 5,023,082

[45] Date of Patent: Jun. 11, 1991

[54] SUSTAINED-RELEASE PHARMACEUTICAL COMPOSITIONS

[75] Inventors: Michael Friedman; Doron Steinberg; Aubrey Soskolne, all of Jerusalem, Israel

[73] Assignee: Yissum Research Development Company of the Hebrew University of Jerusalem, Jerusalem, Israel

[21] Appl. No.: 175,623

[22] Filed: Mar. 30, 1988

Related U.S. Application Data

[63] Continuation-in-part of Ser. No. 49,255, May 13, 1987, abandoned.

[30] Foreign Application Priority Data

May 18, 1986 [IL] Israel ........................ 78826

[51] Int. Cl.$^5$ .................................. A61K 9/00
[52] U.S. Cl. ........................... 424/426; 424/78; 424/432; 424/484; 424/485; 424/486; 424/487; 424/488
[58] Field of Search ............... 424/484, 485, 486, 487, 424/488, 426, 432

[56] References Cited

U.S. PATENT DOCUMENTS

| | | | |
|---|---|---|---|
| 3,921,636 | 11/1975 | Zaffaroni | 424/425 X |
| 3,933,025 | 1/1976 | Whitaker et al. | 424/16 |
| 4,169,885 | 10/1979 | Raaf | 424/16 |
| 4,277,364 | 7/1981 | Shasha | 252/316 |
| 4,279,812 | 7/1981 | Cioca | 424/426 X |
| 4,307,717 | 12/1981 | Hymes et al. | 128/156 |
| 4,344,857 | 8/1982 | Shasha | 252/316 |
| 4,349,530 | 9/1982 | Royer | 424/426 |
| 4,359,483 | 11/1982 | Kaetsu et al. | 427/2 |
| 4,442,655 | 4/1984 | Stroetmann | 424/423 X |
| 4,492,684 | 1/1985 | Goosen et al. | 424/19 |
| 4,517,006 | 5/1985 | Drake et al. | 424/426 X |
| 4,568,536 | 2/1986 | Kronenthal et al. | 424/484 X |
| 4,569,837 | 2/1986 | Suzuki et al. | 514/902 X |
| 4,675,381 | 6/1987 | Bichon | 424/426 X |
| 4,678,516 | 7/1987 | Alderman | 106/197.1 |
| 4,703,108 | 10/1987 | Silver et al. | 424/485 X |
| 4,794,002 | 12/1988 | Henis et al. | 424/485 X |
| 4,803,075 | 2/1989 | Wallace et al. | 424/423 |

FOREIGN PATENT DOCUMENTS

2319852 10/1973 Fed. Rep. of Germany.

*Primary Examiner*—Thurman K. Page
*Attorney, Agent, or Firm*—Sterne, Kessler, Goldstein & Fox

[57] ABSTRACT

The present invention pertains to biodegradable sustained-release compositions capable of achieving the sustained release of a pharmaceutical or other agent. The compositions can be formed into implant devices which may be used to treat a wide variety of diseases and conditions. The implants are especially useful in treating diseases such as periodontal disease which require prolonged drug release.

42 Claims, No Drawings

SUSTAINED-RELEASE PHARMACEUTICAL COMPOSITIONS

CROSS-REFERENCE TO RELATED APPLICATIONS

This application is a continuation-in-part of U.S. patent application Ser. No. 049,255, filed on May 13, 1987 now abandoned.

FIELD OF THE INVENTION

The present invention pertains to sustained-release compositions, suitable for achieving the sustained release of pharmaceutical or other agents. The invention more specifically concerns a biodegradable composition which may be employed in the treatment of periodontal disease.

BACKGROUND OF THE INVENTION

A. Periodontal Disease

The two major diseases of the oral cavity are dental caries, a disease process by which cavities are produced in the tooth surface, and periodontal disease, a process in which the bone and soft tissues supporting the tooth are destroyed. Periodontal diseases are a very common occurrence affecting, at a conservative estimate, between 70-90% of the world population and is the major cause of tooth loss in people over 35 years of age.

Periodontal disease is an all-inclusive term for a variety of clinical conditions that are forms of either gingivitis or periodontis. Gingivitis is an inflammation of the gingiva (or gums) that can be associated with poor oral hygiene and/or the hormonal state of the patient. It is believed that gingivitis, if untreated, will develop into periodontis. Periodontis is a bacterial disease in which the infection has progressed to involve the oral tissues which retain the teeth in the jawbone. Periodontis, if untreated, will eventually result in the loss of the affected tooth.

Although dental caries may be effectively treated with a combination of proper hygiene and fluoride, periodontal disease is often more refractile to treatment. This difference in amenability to treatment reflects the markedly different environments of the oral and periodontal cavities. The oral cavity is essentially an aerobic environment, which is constantly perfused by saliva. In contrast, the periodontal microenvironment is more anaerobic and is perfused by a plasma filtrate, known as the "gingival crevice fluid." The growth of microorganisms within this microenvironment has been shown to be the cause of periodontal disease (Loe, et al., J. Periodontol. 36:177 (1965); Slots, Scand. J. Dent. Res., 85:247 (1977); Socransky, S.S., J. Periodontol. 48:497-504 (1977); Axelsson, P., et al., J. Clin. Periodon. 5:133-151 (1978)). Hence, the treatment of the disease is directed toward controlling this growth. As the periodontal disease becomes more established, the periodontal microenvironment becomes more anaerobic and the flow of gingival crevice fluid increases. An excellent review of periodontal disease, and the methods for its treatment, is provided by Goodson J.M. (In: Medical Applications of Controlled Release, Vol. II, Applications and Evaluation (Langer, R.S., et al., Eds.), CRC Press, Inc., Boca Raton, FL (1984), pp. 115-138), which reference is incorporated by reference herein.

Efforts to treat periodontal disease have been impeded by several factors. Because the site of the bacterial infection is largely inaccessible to agents present in the oral cavity, antimicrobial agents provided to the oral cavity are generally ineffective. The increased flow of gingival crevice fluid, which accompanies periodontal disease, has the effect of diluting and removing therapeutic agents placed within the periodontal crevice. Systemic administration of antibiotics has been shown to be a useful method of controlling the subgingival flora (Listgarten et al., J. Clin. Periodont. 5:246 (1978)), however discontinuation of therapy is often associated with the return of the potential pathogens to the pockets. Systemic administration, therefore, has had only variable success in treating periodontal disease (Genco, R.J., J. Periodontol. 52:545 (1981)). Long-term antibacterial therapy has been used, but the potential dangers associated with this form of treatment, which include the development of resistant strains and super-imposed infections, do not warrant its serious consideration. Antibacterial agents such as chlorhexidine and quaternary ammonium salts in the form of mouth rinses have proved to be successful in preventing periodontal disease (Loe et al., J. Periodont. Res. 5:78 (1970)). These agents, however, are unable to affect the subgingival flora when administered in this form as they do not penetrate into the pockets which are the result of the disease. Hence, they cannot be used in mouth rinses to treat an established periodontal disease.

Patient acceptance has significantly limited the utility of non-pharmacological treatments of periodontal disease. The most widely used non-pharmacological approach to date has been mechanical cleaning methods combined with surgery. Although this method has proved to be fairly successful in treating individuals, there is still a high recurrence rate. There is also the problem of motivating people to good oral hygiene habits that they will maintain throughout their lives.

B. Use of Sustained-release Pharmaceutical Compositions in the Treatment of Periodontal and Other Diseases In response to the importance of treating periodontal disease, and the failure of conventional control therapies, researchers have developed control-release pharmaceutical compositions which are capable of being inserted into the periodontal cavity and of slowly releasing an antimicrobial agent. Goodsen et al. (J. Clin. Periodont. 6:83 (1979); J. Periodont. Supp.-Special Issue 81-87 (1985)) proposed the use of a device that could be placed within the pockets and that would provide a sustained release of antibacterial agents to control the pocket flora. The system they described released the drug for up to 10 days. It appeared to cause marked changes in the pocket flora. The most investigated systems for controlled release comprise incorporating such a drug into a polymeric matrix, which is then shaped into a convenient form and implanted into the periodontal cavity.

Ethyl cellulose has been successfully employed as a polymeric matrix of a periodontal implant (Friedman, M., et al., J. Periodon. Res. 17:323-328 (1982); Soskolne, A., et al., J. Periodon. Res. 18:330-336 (1983); Stabholz, A., et al., J. Clin. Periodon. 13:783-788 (1986)). Various antibacterial agents, such as chlorhexidine, metronidazole, iodine, cetyl puridinium chloride, have been incorporated into such ethyl cellulose films. Loesche, W.J. (U.S. Pat. No. 4,568,535) discloses the use of periodontal implants composed of ethyl cellulose which contain metronidazole in the treatment of periodontal disease.

Although such films were found to be effective in treating periodontal disease, their non-biodegradable nature required their removal after the conclusion of therapy.

The usefulness of silicon rubbers as an implant material is well established (Folkman, J., et al., Ann. N. Y. Acad. Sci. 111:857 (1964)). However, even though such polymers are well tolerated by the tissue and are useful for a variety of drugs, their suitability as implants is seriously limited because the device must be surgically removed after use. Hence, a major therapeutic goal is the development of a biodegradable implant which would not need to be removed from the patient.

Degradable polymers and copolymers which have been substantially investigated as potential implant compositions include poly(lactic acid) (Kulkarni et al., Arch. Surg. 93:839 (1966)), poly(glycolic acid) (Miggins, U.S. Pat. No. 2,676,995 (1954)), and poly(lactic acid)-poly(glycolic acid) copolymer (Schmitt et al., U.S. Pat. 2,397,033 (1967)). The properties and uses of such polyamides and of copolymers of polyamides and polyesters have been extensively disclosed (Kurtz, French Patent No. 2,059,690 (1971); Kurtz, French Patent No. 2,059,691 (1971); Mori et al., Japanese Patent No. 72-43,220 (1972); Kurtz, U.S. Pat. No. 3,642,003 (1970)). The biodegradation of poly(lactic acid) and poly(glycolic acid) can require three to five months (Schneider, French Patent No. 1,478,694 (1967); Darkik, Am. J. Surg. 121:656 (1971)). Thus, it would not be preferable to employ implants composed of such polymers in situations where more rapid biodegradation is desired.

Absorbable periodontal implants have been described by Noguchi, et al. (Bull. Tokyo, Med. Dent. Univ. 31:145 (1984)), which used a hydroxypropylcellulose polymer. Suzuki, Y., et al. (U.S. Pat. No. 4,569,837) discloses the use of water-soluble polymeric substances (such as methyl cellulose, gelatin, etc.) as a polymeric matrix for a periodontal implant.

Pharmaceutical compositions containing gelatin have been described by Lieb, H., et al. (U.S. Pat. No. 2,961,374) and by Easton, I.A. (U.S. Pat. No. 4,344,967).

Despite the existence of the above-described sustained drug release compositions, a need still exists for a biodegradable sustained-release composition which is capable of delivering a pharmacological composition for a period of time sufficient to treat a periodontal infection.

SUMMARY OF THE INVENTION

The present invention relates to pharmaceutical compositions suitable for implantation into the periodontal crevice and capable of treating periodontal or other disease.

In detail, the invention comprises a sustained-release composition for permitting the sustained release of an active agent which comprises a polymeric matrix containing a plasticizing agent, and the active agent, wherein the polymeric matrix comprises a cross-linked, water-insoluble protein.

The invention further pertains to a sustained-release composition for permitting the sustained release of a pharmacological agent which comprises a polymeric matrix containing a plasticizing agent, and the active agent, wherein the polymeric matrix comprises a cross-linked, water-insoluble protein, and wherein the pharmaceutical composition additionally contains a cross-linking agent.

The invention is further directed toward a method of administering a pharmacological agent to a patient in need of such an agent, which comprises administering to the patient either of the above two compositions, wherein the active agent of the composition is the pharmacological agent.

The invention further includes a method for treatment for a condition which comprises providing to a patient in need of such treatment either of the above two pharmaceutical compositions, wherein the pharmaceutical composition contains a pharmacological agent capable of providing the treatment and is present in an amount sufficient to impart therapeutic effect to the composition.

DESCRIPTION OF THE PREFERRED EMBODIMENTS

The sustained-release pharmaceutical compositions of the present invention are polymeric solids which may be cast as films, pellets, granules, cubes, cylinders, etc. The equivalent terms "device," "implant," and "sustained-release composition" and "composition" are intended to refer to such polymeric solids. Typically, such sustained-release compositions are formed through the solidification of a liquid precursor described herein as a "liquid composition."

The sustained-release compositions of the present invention may be formulated to contain a pharmacological agent, and thus have utility in treating or preventing disease in both animals and humans. Such pharmacological agents may include any of a wide variety of pharmaceuticals or biologicals.

The sustained-release compositions of the present invention also have numerous applications in agriculture. For example, such compositions may contain herbicides or pesticides (such as insecticides or antihelminth agents, etc.), as well as animal repellents or attractants. Similarly, such compositions may contain fertilizers or other growth nutrients.

The sustained-release compositions of the present invention may be formulated to contain enzymes, or substrates or products of enzymes, and thus have utility in immobilized enzyme bioreactors. Additionally, such implants may be used to provide enzymes, substrates, or products of enzymes to individuals over a sustained time period.

The nature of the preferred components of the sustained-release compositions of the present invention is described in greater detail below.

I. THE COMPONENTS OF THE PHARMACEUTICAL COMPOSITIONS OF THE PRESENT INVENTION

A. THE POLYMERIC MATERIAL OF THE COMPOSITION

In order to provide a biodegradable polymeric matrix for the sustained release of a drug or agent, it is preferable to employ a polymeric matrix composed of cross-linked protein. Suitable polymers include proteins derived from connective tissue (such as gelatin and collagen), albumin proteins (such as serum albumin, milk albumin, soy albumin, etc.), enzymes (such as papain, chymotrypsin, etc.), serum proteins (such as fibrinogen), and the proteolytic degradation products of bacterial, plant, or animal cells (i.e., tryptone, peptone, etc.). It is not necessary to employ a single protein; thus, the compositions of the present invention may contain two or more different proteins. The present invention does not require the use of protein having a specific level of purity. Thus, protein of any grade of purity may be employed. It is, however, preferable to employ protein having a high degree of purity, and especially preferable to employ protein having a defined (i.e., specifiable) composition, since the use of such proteins increases the degree with which the release of the pharmaceutical agent may be controlled. Thus, it is more preferable to employ a protein such as gelatin or albumin, than a proteolytic degradation product such as tryptone.

Although any of a variety of proteins may be employed, it is preferable to employ gelatin, and most preferable to employ a gelatin which has been partially hydrolyzed by enzymatic action. The molecular weight of the preferred partially hydrolyzed gelatin is preferably between 1,000–12,000 d. Byco ® proteins (a trademark of Croda Colloids, Ltd.) and in particular Byco ® E, C, A, and O. have been found to be the most preferred proteins for use as the polymeric matrix of the present invention. The molecular weights of these proteins range from about 7,600 d to about 50,000 d.

B. THE CROSS-LINKING AGENT OF THE COMPOSITIONS

To be effective in treating (i.e., reversing the progress of, or eliminating) or preventing a disease such as periodontal disease or other bacterial or fungal infections, it is necessary that the sustained-release compositions of the present invention be maintained for a prolonged period of time (i.e., 2–10 days). Since the above-described polymeric materials are water-soluble, they will, if unaltered, dissolve too rapidly to provide an effective therapy for a disease such as periodontal disease or other bacterial or fungal infections. To render such compositions suitable for use in the present invention, it is desirable to treat the compositions in a manner which will make them water-insoluble. Any means capable of accomplishing this goal may be employed; however, it is preferable to employ an agent which is capable of cross-linking protein chains.

Suitable cross-linking agents include aldehydes (such as formaldehyde, glutaraldehyde, etc.), alcohols, di-, tri-, or tetravalent ions (such as aluminum, chromium, titanium, or zirconium ions), acyl chlorides (such as sepacoyl chloride, tetraphthaloyl chloride), or agents such as bis-diazobenzidine, phenol-2,4-disulfonyl chloride, 1,5-difluoro-2,4-dinitrobenzene, urea, 3,6-bis(mercurimethyl)-dioxane urea, dimethyl adipimidate, N,N'-ethylen-bis-(iodoacetamide).

In addition to the above-described chemical agents, any physical means capable of producing cross-links in proteins may alternatively be employed. Such means include heat, pressure, or radiation. The type and the amount of cross-linking agent will control both the rate of release of the drug and the rate of degradation of the device. Thus, increasing the extent of cross-linking increases the duration of the implant and decreases the rate of drug release. Since the cross-linked protein polymer is no longer water-soluble, its degradation is mediated by chemical degradation or through the action of proteolytic enzymes normally present at the site of implantation.

C. THE PLASTICIZING AGENT OF THE SUSTAINED-RELEASE COMPOSITIONS

To improve the flexibility of the sustained-release device, a plasticizing agent is preferably added. Examples of suitable plasticizing agents include phthalate esters, phosphate esters, glycol derivatives, hydrocarbons, oils, or fatty acids. Glycerin and sorbitol have been found to be preferred plasticizing agents. The most preferred plasticizing agent is glycerin. The type and amount of plasticizing agent incorporated into the composition will control the flexibility of the implant.

D. THE PHARMACOLOGICAL OR OTHER AGENT OF THE COMPOSITIONS

As discussed above, a large variety of pharmacological or other active agents may be incorporated into the compositions of the present invention. An agent is said to be "active" if it contributes to the desired therapeutic, agricultural, or catalytic property of the composition. Examples of active agents include pharmacological agents or agricultural products such as herbicides, pesticides, fertilizers, etc. Generally, the amount of drug necessary to obtain the desired therapeutic effect will vary, depending upon the particular drug used and its therapeutic usage. Similarly, the amount of fertilizer, pesticide, herbicide, etc., contained in the compositions will be determined by a consideration of factors such as: the desired duration of release, the release kinetics of the agent, the desired concentration of the released agent, etc.

Suitable drugs which can be administered using the sustained-release compositions of the present invention include drugs belonging to the following groups of therapeutic agents:

analgesics such as codeine, morphine, meperidine, phenazocime, propoxyphene pentazocine and the like;

anti-arrhythmic drugs such as quinidine, lidocaine, procainamide, disopyramide and the like;

anti-bacterial agents such as sulfonamides, phenolics, mercurials, quarternary ammonium compounds, chlorhexidine and the like;

antibiotics such as penicillins, cephalosporins, tetracyclines, oxytetracyclines, chlorotetracycline, metronidazole, chloramphenicol, streptomycin, neomycin, as well as antiviral agents (such as AZT, substituted nucleosides, etc.) and the like;

anti-convulsant agents such as phenytoin, methsuximide, phenazepam, carbamazepine, ethotoin, clonopin and the like;

anti-fungal agents, such as nystatin, griseofulvin, and the like;

anti-pyretic agents and anti-inflammatory agents, such as aspirin, salicylamide, naproxen, indomethacin, fenoprofen, indoprofen, diclofenac, carprofen and the like;

anti-inflammatory agents;

anti-tumor agents such as 5-fluorouracil, floxuridine, cyclophosphamide, estramustine phosphate cytosine, arabinoside and the like;

anti-ulcer drugs such as cimetidine, ranitidine and the like;

cardiovascular drugs, such as nitroglycerin, amyl nitrite, pentaerythritol tetranitrate, isosorbide dinitrate, pyridamole, propranolol, digitalis, digitoxin, digoxin and the like;

diuretics, e.g., benzthiazide, chlorothiazide, hydrochlorothiazide, cyclothiazide, flumethiazide, furosemide, thiamterene, ethacrynic acid, bumetanide, and the like;

hormones, such as insulin, thyroxin, progesterone, testosterone, estrogen, chorionic gonadotropin, and the like;

hypoglycemic drugs such as the thiazides and the like;

hypotensive drugs such as hydralazine and the like;

ophthalmocological agents, such as antibacterials, anti-glaucomatous agents (for example, dichlorphenamide, isofluorophate, etc.), antiviral agents (for example, vidarabine, etc.), steroids (for example, dexamethasone, prednisolone, etc.), and the like;

sedatives and hypnotics, e.g., barbiturates such as phenobarbital, sodium phenobarbital, and the like; chloral hydrate; glutethimide, methylprylon methaqualone and the like; and tranquilizers, such as chloropromazine, promazine, prochlorperazine, reserpine, meprobamate, benzodiazepines, such as chlordiazepoxide, diazepam, oxazepam, bromazepam and the like.

Suitable non-pharmacological agents which can be administered using the sustained-release compositions of the present invention include compounds belonging to the following groups:

fertilizers, such as nitrates, phosphates, chelated iron, and the like;

herbicides, such as the chlorinated phenoxyalkanoic acids, s-Triazines, carbamates, phenylureas, chloroacetamides, glyphosat, and the like;

pesticides, such as insecticides (for example, organophosphorus compounds, cyclodienes, difluorobenzuron, allethrin, resmethrin, ryania, and carbamate insecticides, etc.) or anti-helminth agents (for example, fenbendazole, KT-199, ivomectin, albendazole, etc.);

insect attractants, such as pheromones and the like;

insect repellents, such as substituted toluamides, and the like.

The sustained-release compositions of the present invention may be used to achieve the sustained release of enzymes, enzyme substrates, or enzyme products. Suitable enzymes include transaminases, superoxide dismutases, catalases, beta-galactosidases, phosphatases, peroxidases, peptidases, lipases, carbohydratehydrolizing enzymes, and the like.

II. FORMULATION OF THE SUSTAINED-RELEASE COMPOSITIONS OF THE PRESENT INVENTION

It is possible to mix the above-described components in any ratio which is capable of producing a liquid composition which, when dried, forms a sustained-release composition. The desired characteristics of such a sustained-release composition include flexibility, biodegradability, sustained retention, and the capacity to permit the release of an active agent. The components of the sustained-release drug delivery implants may be mixed as liquids, or as solids to be dissolved in a suitable solvent. Especially suitable solvents include water, ethanol, and water-ethanol mixtures.

It is preferable to prepare the sustained-drug release compositions of the present invention by pouring a liquid form of the present invention (i.e., a liquid composition) into molds which may then be dried. If the concentration of protein used in the liquid composition is too high, it will affect the pourability of the liquid composition. If the protein concentration is too low, the release rate of the sustained-release composition will be too rapid. This excessive drug release rate may, however, be lowered through the use of lower concentrations of the active agent. It is, therefore, preferable to employ a protein concentration range which results in the formation of a liquid composition having acceptable pourability, but which, when dried into the sustained-release compositions of the present invention is capable of releasing an active agent over a sustained period of time. The evaporation of solvent results in a loss of both weight and volume, and thus alters the concentration percentages of the components of the pharmaceutical composition. The possible composition of the preparation and the effect of evaporation on the concentration of its components is shown in Table 1.

TABLE 1

EFFECT OF THE EVAPORATION OF SOLVENT ON THE CONCENTRATION OF THE COMPONENTS IN THE SOLIDIFIED PHARMACEUTICAL COMPOSITION

| Components of Pharmaceutical Composition | Liquid State | Approximate Solidified Pharmaceutical Composition (after evaporation of indicated percentage of solvent) | | | |
|---|---|---|---|---|---|
| | | 70% | 80% | 90% | 95% |
| Protein | 1–50 | 1.54–77 | 1.56–83 | 1.68–90.9 | 1.75–95 |
| Cross-Linking Agent | 0.0001–5 | 0.0001–12.3 | 0.0001–15.6 | 0.0001–22 | 0.0001–26 |
| Plasticizing Agent | 0.01–15 | 0.01–31.1 | 0.01–38 | 0.01–47 | 0.01–52 |
| Pharmacological Agent | 0.01–25 | 0.012–46 | 0.013–53 | 0.013–60 | 0.013–66 |

When dried to produce the implants of the present invention, such compositions must have a high enough concentration of protein to produce a non-gel-like material having structural stability. Such suitable compositions can be formulated from a liquid which contains from about 10–50% (by weight) protein. Upon evaporation of about 90% of solvent, such compositions would contain from about 16% to about 91% (w/w) protein. It is preferable that the solidified composition have a flexibility of from about 0.1 kg/mm² to about 50 kg/mm².

When employing Byco ® as the protein polymer, it is preferable to prepare a liquid composition which contains from about 15% to about 30% Byco ® protein and from about 0.0006% to about 0.15% of cross-linking agent, preferably glutaraldehyde. It is preferable to dry such a composition by evaporating the solvent to produce a solid composition having from about 7.5% to about 17.5% w/w of solvent and about 48% to about 83% w/w of cross-linked Byco ® and from about 3.8% to about 21% w/w of plasticizer agent and from about 4% to about 24% w/w of pharmaceutical agent. This material is then incubated in the presence of a cross-linking agent (preferably glutaraldehyde) until a sufficient degree of cross-linking has been obtained.

The plasticizer, which may be added to the above-described solution to control the flexibility of the final dried composition, must be present in an amount sufficient to prevent the final composition from being brittle, or too flexible. The plasticizer must not be present in an amount which prevents the release of the active agent. Thus, such a plasticizer should be present between from about 0.01% to about 15% (w/w) prior to the drying of the compositions. Upon evaporation of about 90% of solvent, such compositions would contain from about 0.010% to about 41% (w/w) plasticizing agent.

The pharmacological agent which may be employed in the composition may be added to the implant by any of several processes. In one embodiment, a powder form of the pharmacological agent is introduced into a liquid composition and permitted to dissolve in situ. In a second embodiment, the pharmacological agent is dissolved in a suitable solvent prior to its addition to a liquid composition. In the above embodiments, the liquid compositions are then dried to form the sustained-release compositions of the present invention. In yet another embodiment, a liquified form of the pharmacological agent is introduced into a solidified implant. Such introduction may be accomplished by immersing the solidified implant in a solution which contains the pharmacological agent, or by placing a suitable amount of the pharmacological agent in contact with the solidified implant and permitting the implant to absorb the pharmacological agent.

The amount of the pharmacological agent added to the implant will vary, in a manner understood by those of ordinary skill in the art, depending upon such criteria as: (1) the desired total dosage, (2) the desired release kinetics, (3) the desired duration of treatment, (4) the desired size of the implant and its intended location, or (5) possible interactions between the pharmaceutical agent of the implant and any other medicament being administered. The above criteria will depend upon such factors as the patient's age, height, weight, sex, medical history, etc. The pharmacological agent must be present in an amount sufficient to impart therapeutic effect to the pharmaceutical composition. The nature of the active agent in the implant also plays an important role in the control release mechanism. For example, a film-like implant containing 20% w/w of chlorhexidine acetate per protein has been found to release this agent more slowly than the same implant containing 20% w/w of tetracycline HCl. Different salts of the same active agent may be released at different rates. For example, chlorhexidine acetate has been found to be released more slowly than chlorhexidine HCl from film-like implants having the same formulation and containing 20% (w/w) chlorhexidine per protein.

In general, the concentration of pharmacological agent will vary from 0.01 mg-2 g per therapeutic treatment. The liquid compositions will, in general, contain between 0.01-25% pharmacological agent (by weight). Upon evaporation of approximately 90% of the liquid solvent, the resulting implant will contain between approximately 0.013-61% pharmacological agent (by weight).

The implants of the present invention may contain only a single pharmacological agent or may contain a combination of two or more pharmacological agents. For example, an implant used in the treatment of periodontal disease may contain several antimicrobial agents or may contain both (i) (one or more) antimicrobial agent(s) and (ii) an analgesic and/or an anti-inflammatory agent.

In a preferred embodiment, the weight ratios of pharmacological agent to protein in the implants will vary from about 0.01:7 (respectively) to about 3:1 (respectively). In a preferred embodiment, the weight ratio of plasticizing agent to protein will vary from about 0.01:7 (respectively) to about 4:7 (respectively).

When a cross-linking agent is to be added to the non-evaporated liquid form of the composition, it should be present in an amount capable of rendering the protein polymer water-insoluble. If, however, excessive amounts of the cross-linking agent are introduced, the resulting implant will have an unacceptably slow drug release rate. Thus, if a cross-linking agent is provided to the liquid composition, it should be provided in an amount sufficient to render the resulting implant insoluble, but not in an amount which prevents the release of the pharmacological agent from the pharmaceutical composition. The action of the cross-linking agent may result in the denaturation of the protein. The degree of denaturation of the protein caused by the cross-linking agent provides a means of controlling the degradability of the films in vivo and in vitro, there being an inverse relationship between the degree of denaturation and the degradability of the implant. The release of the pharmacological agents from the implants can be manipulated by the degree of cross-linking and denaturation of the protein, there being a direct relationship between the degree of cross-linking or denaturation and the rate of release of the active agent from the implant. Depending upon the extent of cross-linking, the implants of the present invention can require between 1-30 days to dissolve.

In general, if one desires to add a cross-linking agent to the liquid composition prior to its drying into the desired implant, the cross-linking agent should be added to the liquid in an amount of from about 0.0001% to about 5% (weight by weight). Upon evaporation of about 90% of solvent, the resulting film would contain from about 0.0001% to about 22% (weight by weight) cross-linking agent.

Although, as described above, it is possible to incorporate a cross-linking agent into the liquid composition which, upon drying, forms the implants of the present invention, it is also possible to dry the liquid compositions, and to then cross-link the protein polymer, The most preferable way of cross-linking is a combination of the method where a partially cross-linked implant is further incubated in the presence of glutaraldehyde vapors. Such treatment is preferable, since it minimizes the time necessary to attain sufficient cross-linking. Sufficient cross-linking is considered to have been achieved when the final implant cannot be dissolved in water within 10 days. The amount of the cross-linking agent which is ultimately incorporated into an implant treated in the above-described manner is extremely small, and results in almost no change in weight.

Any means capable of drying (i.e., solidifying) the liquid compositions of the present invention may be employed. Thus, solidification may be accomplished by evaporating solvent until a desired degree of rigidity is obtained. This evaporation may be accomplished by incubating the liquid compositions at ambient or elevated temperatures, either at atmospheric pressure or in vacuo. Evaporation which occurs in the presence of elevated temperatures, or in vacuo, may result in surface defects (such as air pockets, etc.). Thus, if such defects are undesirable, it is preferable to dry the liquid compositions at ambient temperatures under atmospheric pressure. It is most preferable to form the implants of the present invention by evaporating a liquid composition to form a solidified material. Such evaporation is most preferably conducted at room termperature or temperatures between 40-50° C., at atmospheric pressure.

The above-described evaporation process removes a substantial amount of the solvent initially present in the liquid composition. The sustained-release composition is, however, not completely solvent-free. Thus, in a preferred embodiment in which the solvent is water or a water-ethanol mixture, the implant is hydrated and non-anhydrous. In general, it is desirable to evaporate sufficient solvent to produce a solid, but not so much solvent as to impair the flexibility of the resulting composition. Thus, in general, it is desirable to evaporate between 70–95% of the solvent initially present in the liquid compositions. It is most preferable that the obtained implant will contain about 7.5% to about 17.5% w/w of solvent.

The particular form into which the sustained-release composition is cast will depend upon its intended use. Thus, for example, if the implant is designed to be used in the treatment of periodontal (or other dental) disease by insertion into the gingival crevice, then the implant will preferably be cast into a film or film-like sheet. The term "gingival crevice" is meant to be equivalent to the terms "periodontal crevice," "periodontal cavity," or "periodontal pocket." As such, the term is intended to refer to the space between the tooth and gum of an individual.

In order to be inserted into a patient's periodontal pocket to treat periodontal or other disease, the implant should preferably be a film having a thickness which ranges from 0.01–1.0 millimeters, and preferably having a thickness of between 0.1 and 0.3 millimeters. In order to be inserted in the periodontal pocket, it is preferable that the implant shape be oval and/or torpedo (i.e., bullet). Although the width and length of the implant may vary depending upon the size of the periodontal pocket of the recipient patient, it is preferable to use implants having a width of between 1–5 millimeters, and preferably between 2–4 millimeters. It is preferable to employ implants having a length of between 3–10 millimeters, and most preferable to employ implants having a length of between 5–8 millimeters. Implants having such dimensions, and, therefore, suitable for insertion into the periodontal pocket of a patient may be employed to treat or prevent periodontal disease (as by containing an anti-microbial agent, etc.). As discussed above, the implant may be used to provide any of the large variety of pharmacological agents whose prolonged release may be desired in the treatment of disease. The implants of the present invention may be individually produced or may be obtained (i.e., cut, ground, etc.) from a larger material (i.e., a block, or film-like sheet).

In addition to its use in the treatment of periodontal disease, the sustained-release compositions of present invention may be used in a variety of alternative dental applications. For example, the sustained-release compositions of the present invention may be used in the treatment and/or prevention of pericoronitis. The implants may also be used to assist with root canal sterilization and as an analgestic. Additionally, the sustained-release compositions of the present invention may be used to facilitate the healing of gums after tooth extraction and to treat or prevent the problem of "dry socket." The sustained-release compositions of the present invention may be employed to prevent infection incident to tooth implants or epiectomy.

As disclosed above, it is alternatively possible to prepare an implant of greater thickness or of different dimensions which will not be inserted into the periodontal cavity. The size and shape of such an implant will depend upon (a) the dimensions of the site into which it is to be inserted, (b) the desired duration of therapy, (c) the desired amount and concentration of the pharmacological agent which it contains or (d) the desired drug release kinetics. Such implants may be used to provide sustained drug release for any of a variety of diseases or conditions.

Because the sustained-release compositions of the present invention may contain one or more of a variety of different drugs (such as antibiotics, analgesics, etc.), they may be employed as an adjunct to surgery to prevent or treat post-surgical infection.

The sustained-release compositions of the present invention may be used to treat (or prevent) microbial infections at wounds (either accidental or as a consequence of surgery or other medical treatments), burns, abrasions, etc. Such implants may be used alone, in combination with bandages or dressings, or as an adjunct to other treatments.

Implants that contain anti-tumor agents may be placed at the site of the tumor, thereby providing a therapy for cancer. Implants containing analgesics or antipyretics could be used to alleviate pain or inflammation.

Implants containing cardiovascular drugs or anti-arrhythmic drugs may be used in the treatment of heart disease. In a similar manner, by employing implants which contain a suitable pharmacological agent, it is possible to provide effective therapy for the large variety of diseases that may be treated by a sustained drug therapy regime.

The sustained-release compositions of the present invention may also be employed in conjunction with artificial organs or as an additional part of such an organ. For example, by immobilizing cells within the sustained-release compositions of the present invention, it is possible to create an implant which may serve as an artificial organ.

The pharmaceutical compositions of the present invention may be used in conjunction with implants to facilitate their acceptance by the recipient, or to control infection or inflammation associated with such implants.

The sustained-release compositions of the present invention may be administered to recipients by intranasal, intra-ocular, intra-aural, subcutaneous, transdermal means, or by topical application, or by any other parenteral means.

Having now generally described this invention, the same will be better understood by reference to certain specific examples which are included herein for purposes of illustration only and are not intended to be limiting of the invention, unless specified.

Sustained pharmaceutical implants were prepared according to the procedures described in the following examples.

EXAMPLE 1

1. 9.75 g of Byco E was dissolved in distilled water to make 26 g and allowed to stand.
2. 1.5 g of chlorhexidine acetate was solubilized in 5 ml of absolute ethanol.
3. 20 g of the clear Byco solution was added to the chlorhexidine solution while stirring constantly.
4. 1.0 g of glycerine was added to the solution while stirring constantly.

5. 5 g of the liquid was poured into plastic petri dishes (9.5 cm in diameter).

6. The petri dishes were placed in an evaporator for 48 hours and the liquid was allowed to evaporate.

EXAMPLE 2

1. 9.75 g of Byco E was dissolved in distilled water to make 26 g and allowed to stand.
2. 1.5 g of chlorhexidine acetate was solubilized in 5 ml of absolute ethanol.
3. 20 g of the clear Byco solution was added to the chlorhexidine solution, while stirring constantly.
4. 1.0 g of glycerine was added to the solution while stirring constantly.
5. 50 µl of formaldehyde solution was added slowly to 5 g of the liquid.
6. The liquid was poured into plastic petri dishes (9.5 cm in diameter).
7. The petri dishes were placed in an evaporator for 48 hours and the liquid was allowed to evaporate.

EXAMPLE 3

1. 9.75 g of Byco E was dissolved in distilled water to make 26 g and allowed to stand.
2. 1.5 g of chlorhexidine acetate was solubilized in 5 ml of absolute alcohol.
3. 20 g of the clear Byco solution was added to the chlorhexidine solution while stirring constantly.
4. 1.0 g of glycerine was added to the solution while stirring constantly.
5. 100 µl of formaldehyde solution was added slowly to 5 g of the liquid.
6. The liquid was poured into plastic petri dishes (9.5 cm in diameter).
7. The petri dishes were placed in an evaporator for 48 hours and the liquid was allowed to evaporate.

EXAMPLE 4

1. 9.75 g of Byco E was dissolved in distilled water to make 26 g and allowed to stand.
2. 1.5 g of chlorhexidine acetate was solubilized in 5 ml of absolute alcohol.
3. 20 g of the clear Byco solution was added to the chlorhexidine solution while stirring constantly.
4. 1.0 g of glycerine was added to the solution while stirring constantly.
5. 150 µl of formaldehyde solution was added slowly to 5 g of the liquid.
6. The liquid was poured into plastic petri dishes (9.5 cm in diameter).
7. The petri dishes were placed in an evaporator for 48 hours and the liquid was allowed to evaporate.

EXAMPLE 5

1. 9.75 g of Byco E was dissolved in distilled water to make 26 g and allowed to stand.
2. 1.5 g of chlorhexidine acetate was solubilized in 5 ml of absolute ethanol.
3. 20 g of the clear Byco solution was added to the chlorhexidine solution while stirring constantly.
4. 1.0 g of glycerine was added to the solution while stirring constantly.
5. 200 µl of formaldehyde solution was added slowly to 5 g of the liquid.
6. The liquid was poured into plastic petri dishes (9.5 cm in diameter).
7. The petri dishes were placed in an evaporator for 48 hours and the liquid was allowed to evaporate.

The following examples were prepared using the same procedure as that described above—amounts are in grams unless indicated otherwise and refer to the liquid compositions.

EXAMPLE 6

| | |
|---|---|
| Byco E | 7.5 |
| Water ad | 20 |
| Glycerine | 1.0 |
| Chlorhexidine acetate | 0.75/5 ml Ethanol |
| Formaldehyde | 100 µl/5 g |

EXAMPLE 7

| | |
|---|---|
| Byco E | 7.5 |
| Water ad | 20 |
| Glycerine | 1.0 |
| Chlorhexidine acetate | 3.0/5 ml ethanol |
| Formaldehyde | 100 µl/5 g |

EXAMPLE 8

| | |
|---|---|
| Byco E | 7.5 |
| Water ad | 20 |
| Glycerine | 1.0 |
| Chlorhexidine acetate | 4.5/5 ml Ethanol |
| Formaldehyde | 100 µl/5 g |

EXAMPLE 9

| | |
|---|---|
| Byco E | 7.5 |
| Water ad | 20 |
| Glycerine | 1.0 |
| Chlorhexidine HCl | 0.75 |
| Formaldehyde | 100 µl/5 g |

EXAMPLE 10

| | |
|---|---|
| Byco E | 7.5 |
| Water ad | 25 |
| Glycerine | 1.0 |
| Chlorhexidine HCl | 1.5 |
| Formaldehyde | 100 µl/5 g |

EXAMPLE 11

| | |
|---|---|
| Byco E | 7.5 |
| Water ad | 25 |
| Glycerine | 1.0 |
| Chlorhexidine HCl | 3.0 |
| Formaldehyde | 100 µl/5 g |

EXAMPLE 12

| | |
|---|---|
| Byco E | 7.5 |
| Water ad | 25 |
| Glycerine | 1.0 |
| Chlorhexidine HCl | 4.5 |
| Formaldehyde | 100 µl/5 g |

EXAMPLE 13

| | |
|---|---|
| Byco E | 7.5 |
| Water ad | 25 |

-continued
EXAMPLE 13

| | |
|---|---|
| Glycerine | 1.0 |
| Tetracycline | 1.5 |
| Formaldehyde | 100 μl/5 g |

EXAMPLE 14

| | |
|---|---|
| Byco E | 7.5 |
| Water ad | 25 |
| Glycerine | 1.0 |
| Tetracycline HCl | 1.5 |
| Formaldehyde | 50 μl/5 g |

EXAMPLE 15

| | |
|---|---|
| Byco E | 7.5 |
| Water ad | 25 |
| Glycerine | 1.0 |
| Tetracycline HCl | 1.5 |
| Formaldehyde | 100 μl/5 g |

EXAMPLE 16

| | |
|---|---|
| Byco E | 7.5 |
| Water ad | 25 |
| Glycerine | 1.0 |
| Tetracycline HCl | 1.5 |
| Formaldehyde | 200 μl/5 g |

EXAMPLE 17

| | |
|---|---|
| Byco E | 7.5 |
| Water ad | 25 |
| Sorbitol | 0.0034 |
| Chlorhexidine acetate | 1.5/5 ml ethanol |
| Formaldehyde | 200 μl/5 g |

EXAMPLE 18

| | |
|---|---|
| Byco E | 7.5 |
| Water ad | 25 |
| Sorbitol | 0.5 |
| Chlorhexidine acetate | 1.5/5 ml ethanol |
| Formaldehyde | 200 μl/5 g |

EXAMPLE 19

| | |
|---|---|
| Byco E | 7.5 |
| Water ad | 25 |
| Sorbitol | 1.5 |
| Chlorhexidine acetate | 1.5/5 ml ethanol |
| Formaldehyde | 200 μl/5 g |

Sustained pharmaceutical implants were prepared according to the procedures described in the following examples.

EXAMPLE 20

1. 7.5 g of gelatin were dissolved in 39.0 ml of hot distilled water.
2. 0.75 g of chlorhexidine acetate was solubilized in 5.0 ml of ethyl alcohol.
3. The alcohol solution was added to the aqueous solution.
4. 5 g of the liquid was poured into petri dishes, diameter 9.5 cm.
5. The petri dishes were placed in an evaporator for 48 hours and the liquid was allowed to evaporate.

EXAMPLE 21

1. 7.5 g of gelatin were dissolved in 39.0 ml of hot distilled water.
2. 0.75 g of chlorhexidine acetate was solubilized in 5.0 ml of ethyl alcohol.
3. The alcohol solution was added to the aqueous solution.
4. 50 μl of formaldehyde was added slowly to 5 g of the liquid.
5. The liquid was poured into petri dishes (9.5 cm in diameter).
6. The petri dishes were placed in an evaporator for 48 hours and the liquid was allowed to evaporate.

EXAMPLE 22

1. 7.5 g of gelatin Were dissolved in 39.0 ml of hot distilled water.
2. 0.75 g of chlorhexidine acetate was solubilized in 5.0 ml of ethyl alcohol.
3. The alcohol solution was added to the aqueous solution.
4. 100 μl of formaldehyde was added slowly to 5 g of the liquid.
5. The liquid was poured into petri dishes (9.5 cm in diameter).
6. The petri dishes were placed in an evaporator for 48 hours and the liquid was allowed to evaporate.

EXAMPLE 23

In vitro release tests

Films were prepared by evaporating approximately 80% of the solvent from the compositions of the preceding examples.

The casted films were carefully cut into squares of 1×1 cm dimension. The thickness of each film was measured in five different places on the film, using a micrometer gauge. The average thickness of the films was 200 microns.

The films were placed in distilled water at 37° C. with constant shaking at 100 rpm. The solutions were circulated through a flow cell of a U.V. spectrophotometer, using a peristaltic pump. The amount of active ingredient released from the film was measured at 254 nm for chlorhexidine/protein or at 275 nm for tetracycline or tetracycline HCl. The results of this experiment are shown in Tables 2-5.

TABLE 2

RELEASE OF CHLORHEXIDINE ACETATE FROM FILMS CONTAINING 20% W/W CHLORHEXIDINE

| Time (hours) | % of Release | | | |
|---|---|---|---|---|
| | Example 1 | Example 2 | Example 3 | Example 5 |
| 1 | 81 | 14 | 6 | 2 |
| 2 | 89 | 23 | 14 | |
| 3 | 100 | 31 | 21 | 6 |
| 4 | | 38 | 27 | |
| 5 | | 44 | 33 | |
| 6 | | 51 | 38 | 13 |
| 7 | | 56 | 41 | |
| 8 | | 61 | 48 | |
| 9 | | 66 | 52 | 18 |
| 10 | | 70 | 56 | |

TABLE 2-continued

RELEASE OF CHLORHEXIDINE ACETATE FROM
FILMS CONTAINING 20% W/W CHLORHEXIDINE

% of Release

| Time (hours) | Example 1 | Example 2 | Example 3 | Example 5 |
|---|---|---|---|---|
| 12 |  | 81 | 64 | 22 |
| 14 |  | 89 | 70 |  |
| 16 |  | 95 | 76 |  |
| 18 |  | 94 | 81 | 33 |
| 20 |  | 100 | 84 |  |
| 25 |  |  | 87 |  |
| 30 |  |  | 91 | 50 |
| 35 |  |  | 93 |  |
| 40 |  |  | 95 |  |
| 45 |  |  | 96 | 57 |
| 50 |  |  | 97 |  |
| 55 |  |  | 99 |  |
| 60 |  |  | 100 | 63 |
| 90 |  |  |  | 75 |
| 120 |  |  |  | 81 |
| 150 |  |  |  | 90 |

Example 1: 0 μl formaldehyde/5 g
Example 2: 50 μl formaldehyde/5 g
Example 3: 100 μl formaldehyde/5 g
Example 5: 200 μl formaldehyde/5 g

TABLE 3

RELEASE OF CHLORHEXIDINE ACETATE/PROTEIN
FROM FILMS CONTAINING 10%, 40%, 60% W/W
CHLORHEXIDINE

% of Release

| Time (hours) | Example 6 | Example 7 | Example 8 |
|---|---|---|---|
| 1 | 9 | 46 | 65 |
| 2 | 14 | 53 | 67 |
| 3 | 22 | 60 | 71 |
| 4 | 31 | 64 | 74 |
| 5 | 39 | 71 | 77 |
| 6 | 49 | 75 | 81 |
| 7 | 59 | 80 | 84 |
| 8 | 67 | 84 | 86 |
| 9 | 74 | 88 | 89 |
| 10 | 80 | 90 | 91 |
| 15 | 94 | 94 | 97 |
| 20 | 97 | 96 | 100 |
| 25 | 100 | 97 |  |
| 30 |  | 98 |  |
| 40 |  | 99 |  |
| 50 |  | 100 |  |

Example 6: 10% w/w chlorhexidine acetate
Example 7: 40% w/w chlorhexidine acetate
Example 8: 60% w/w chlorhexidine acetate

TABLE 4

RELEASE OF CHLORHEXIDINE HCl/PROTEIN FROM
FILMS CONTAINING 10%, 20%, 40%, 60%
CHLORHEXIDINE

% of Release

| Time (hours) | Example 9 | Example 10 | Example 11 | Example 12 |
|---|---|---|---|---|
| 1 | 55 | 51 | 25 | 18 |
| 2 | 87 | 85 | 51 | 37 |
| 3 | 94 | 96 | 73 | 55 |
| 4 | 100 | 99 | 87 | 69 |
| 5 |  | 100 | 93 | 80 |
| 6 |  |  | 95 | 88 |
| 10 |  |  | 98 | 98 |
| 14 |  |  | 99 | 99 |
| 17 |  |  | 100 | 100 |

Example 9: 10% w/w chlorhexidine HCl
Example 10: 20% w/w chlorhexidine HCl
Example 11: 40% w/w chlorhexidine HCl
Example 12: 60% w/w chlorhexidine HCl

TABLE 5

RELEASE OF TETRACYCLINE HCl

% of Release

| Time (hours) | Example 15 | Example 16 |
|---|---|---|
| 1 | 55 | 51 |
| 2 | 76 | 69 |
| 3 | 91 | 83 |
| 4 | 97 | 92 |
| 7 | 98 | 97 |
| 10 | 100 | 100 |

Example 15: 100 μl formaldehyde/5 g
Example 16: 200 μl formaldehyde/5 g

EXAMPLE 24

INHIBITION OF ORAL BACTERIAL GROWTH
IN VITRO

Films were prepared using the compositions of Examples 1–4. The films were cut into circles and placed on Iso-sensitest agar plates seeded with the oral bacteria *Streptococcus mutans*. After incubating at 37° C. for 24 hours, the films were removed from the agar plates and placed on fresh plates seeded with *Streptococcus mutans* and incubated further for 24 hours. This procedure was repeated until no inhibition of bacterial growth was observed. The area of inhibition of growth around the films was measured. The results of this experiment are shown in Table 6.

TABLE 6

INHIBITION GROWTH AREA (%)

| Day | Example 1 | Example 2 | Example 3 | Example 4 |
|---|---|---|---|---|
| 1 | 100 | 100 | 77 | 38 |
| 2 | 84 | 47 | 100 | 61 |
| 3 | 50 | 60 | 46 | 49 |
| 4 | 39 | 40 | 82 | 100 |
| 6 | 0 | 20 | 50 | 32 |
| 10 |  | 21 | 27 | 26 |
| 11 |  | 0 | 32 | 26 |
| 15 |  |  | 25 | 13 |
| 20 |  |  | 20 | 20 |
| 24 |  |  | 13 | 12 |
| 29 |  |  | 0 | 0 |

EXAMPLE 25

A sustained-release composition composed of chlorhexidine and Byco E protein and suitable for use as a periodontal implant was prepared in a preferred manner by incubating the non or the partially cross-linked films in the presence of a vapor containing a cross-linking agent. Films prepared in such a manner can be considered to have the following eight stages:

Stages in the Formation of the Film

1. Byco E is dispersed into a solution.
2. The solution is allowed to clear.
3. Chlorhexidine acetate is added to 5 ml of ethanol supplemented with glycerine. The solution is mixed for 10 minutes.
4. The Byco solution and the chlorhexidine solution are mixed together at 35° C. for 10 minutes.
5. Glutaraldehyde is added to 6.0 g of the above solution.
6. The mixture is poured into molds.
7. The solvent is allowed to evaporate from the mixture, thus forming a thin film.
8. The obtained film is placed in an atmosphere of glutaraldehyde vapor.

In producing the above film, the following considerations were made at the indicated stages:

Stage 1 a. The range of Byco ® protein in the solution is 10%–60% w/w.
b. The Byco ® is dissolved in bidistilled water, buffered to pH range of 3.0–9.0.
c. Rose bengal is added to the solution concentration of 0.00001–1 mg/ml.

Stage 3 a. 0–6.0 g of chlorhexidine acetate or chlorhexidine is solubilized in ethanol.
b. The active ingredient, e.g., chlorhexidine or its salts, was added to the Byco ® solution in the form of a solid powder.

Stage 7

The solvent is evaporated at a range of temperature of 20° C.–60° C.

Stage 8

The obtained films are placed in an atmosphere of glutaraldehyde for 0–72 hours at a range of temperature of 20° C.–60° C.

Characteristics of the obtained film:
1. Concentration of water: 5–30% w/w
2. Concentration of cross-linked Byco ®: 14–95% w/w
3. Concentration of chlorhexidine or chlorhexidine acetate: 0–66% w/w
4. Concentration of glycerin: 0–52% w/w

EXAMPLE 26

The steps of a preferred method for producing the periodontal implant of the present example are provided below:

1. 7.5 g Byco ® E was dispersed in a bidistilled water to make 22.0 g.
2. The mixture was allowed to clear.
3. 1.5 g of chlorhexidine acetate was added to 5 ml of ethanol absolute, supplemented with 1.3 g glycerine. The solution was mixed for 10 minutes.
4. The Byco ® and chlorhexidine solutions were mixed together at 35° C. for 10 minutes.
5. 300 μl of glutaraldehyde was added to 5.0 g of the above solution.
6. The mixture was poured into molds.
7. The solvent was allowed to evaporate at room temperature for 48 hours while forming a film.
8. The above-obtained film was placed in an atmosphere of glutaraldehyde vapor for 24 hours.

The obtained films had the following approximate concentrations:

| | | |
|---|---|---|
| 1. | concentration of water | 10% |
| 2. | concentration of Byco$^R$ | 66% |
| 3. | Concentration of Chlorhexidine or chlorhexidine acetate | 13% |
| 4. | concentration of glycerin | 11% |

EXAMPLE 27

Periodontal implants having various proportions of ingredients were prepared in accordance with the procedure of Example 25. The amounts and ingredients used to produce these implants are shown in Table 7.

TABLE 7

FORMULATION FOR PERIODONTAL IMPLANTS

| Implant Formulation Number: | Amount of Ingredient Present in Implant | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Ingredients in Implant (In Grams Unless Indicated Otherwise) | | | | | | | | | | | | | | | |
| Byco E. | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 |
| Water (Ad Amount in Grams) | 22.0 | 22.0 | 22.0 | 22.0 | 22.0 | 35.0 | 35.0 | 35.0 | 35.0 | 27.0 | 27.0 | 27.0 | 27.0* | 27.0* | 27.0* |
| Glycerin | 1.3 | 1.3 | 1.3 | 1.3 | 1.3 | 1.3 | 1.3 | 1.3 | 1.3 | 1.3 | 1.3 | 1.3 | 1.3 | 1.3 | 1.3 |
| Ethanol | 5.0 | 5.0 | 5.0 | — | — | 5.0 | 5.0 | — | — | 5.0 | 5.0 | 5.0 | 5.0 | 5.0 | 5.0 |
| Chlorhexidine Acetate | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |
| Glutaraldehyde 8% (L)/5G | 150 | 200 | 300 | 150 | 150 | 500 | 200 | 400 | 200 | 500 | 500 | 500 | 500 | 500 | 500 |
| Glutaraldehyde Vapours (HRS) | | | | | | | | | | 0 | 4 | 24 | 0 | 4 | 24 |

*Buffer PH 4 instead of bidistilled water or any buffer.

EXAMPLE 28

The in vitro drug release profile of four of the implants produced in Example 25 were determined. The release profiles are presented in Table 8.

TABLE 8

RELEASE PROFILES OF CHLORHEXIDINE IN-VITRO FROM BIODEGRADABLE FILMS (AMOUNT OF DRUG RELEASED IN %)

| Time (hrs) | Implantation Formulation Number | | | |
|---|---|---|---|---|
| | 10 | 11 | 12 | 14 |
| 2.5 | 60 | 37 | 28 | 30 |
| 5 | 62 | 42 | 30 | 33 |
| 24 | 100 | 72 | 53 | 60 |
| 48 | 100 | 78 | 62 | 66 |
| 120 | — | 84 | 70 | — |
| 168 | — | 89 | 73 | 79 |
| 216 | — | 91.5 | 78 | — |
| 288 | — | 92.5 | 78 | — |

EXAMPLE 29

CLINICAL TRIALS

Preliminary clinical trials were conducted on patients with periodontal diseases. Films prepared using the compositions of Examples 1, 2, 3, or 4 were inserted into periodontal pockets of volunteers in order to test the rate of degradation. Films prepared using the compositions disclosed in Example 1 degraded inside the periodontal pocket within four hours. Films prepared using the compositions disclosed in Examples 2 and 3 degraded within 20 hours. The film prepared from the composition of Example 4 degraded within approximately 36 hours.

Further tests were conducted on the effect of degradable films on the microflora of periodontal pockets.

Preliminary clinical studies have shown that there is a sharp decrease in the number of motile bacteria including spirochetes in the periodontal pocket, after treatment with the film. A reduction in the total count of anaerobic bacteria was observed, accompanied by a reduction in the black pigmented Bacteriodes.

Films prepared from the composition of Example 5 were inserted into periodontal pockets. Samples of subgingival flora were taken before and after the treatment. The samples were examined by using Dark Field Microscopy. It was found that after treatment with these films, there was a reduction in the number of motile bacteria. In three pockets, there was 100% decrease in the number of motile bacteria while in another two pockets there was a 75% reduction in the motile bacteria.

As will be realized from the above description and results, the controlled release of an active antibacterial agent into the periodontal pocket is a prefered way of treating periodontal diseases.

The local placement of a device which provides the controlled release of an active agent from a degradable matrix minimizes the need for removal of the device from the periodontal pockets, when the treatment period is over. This minimizes the number of visits to the periodontist as well as the discomfort associated with the removal of the film.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A liquid precursor composition for the preparation of a biodegradable sustained-release composition for the administration of an active agent, wherein said sustained-release composition is formed by solidification of said liquid precursor composition, said liquid precursor composition comprising:
   (1) a plasticizing agent, wherein said plasticizing agent is selected from the group consisting of a phthalate ester, a phosphate ester, a glycol derivative, a hydrocarbon, an oil, and a fatty acid;
   (2) said active agent, wherein said active agent is present in an amount sufficient to impart a desired therapeutic, agricultural, or catalytic property to said sustained-release composition;
   (3) a cross-linking agent, wherein said cross-linking agent is selected from the group consisting of aldehydes, alcohols, aluminum, chromium, titanium, zirconium, an acyl chloride, bis-diazobenzidine, phenol-2,4-disulfonyl chloride, 1,5-difluoro-2,4-dinitrobenzene, urea, 3,6-bis(mercurimethyl)-dioxane urea, dimethyl adipimidate and N,N'-ethylene-bis-iodacetamide; and
   (4) a water-soluble protein which is capable of being cross-linked into a water-insoluble, biodegradable polymeric matrix, wherein said water-soluble protein is present at a concentration sufficient to provide said sustained-release composition with structural stability after being cross-linked, but not at so great a concentration as to render said sustained-release composition (i) incapable of biodegradation or (ii) incapable of permitting the release of said active agent.

2. A biodegradable sustained-release composition for the administration of an active agent, wherein said sustained-release composition comprises:
   (1) a plasticizing agent, wherein said plasticizing agent is selected from the group consisting of a phthalate ester, a phosphate ester, a glycol derivative, a hydrocarbon, an oil, and a fatty acid;
   (2) said active agent, wherein said active agent is present in an amount sufficient to impart a desired therapeutic, agricultural, or catalytic property to said sustained-release composition;
   (3) a cross-linking agent, wherein said cross-linking agent is selected from the group consisting of aldehydes, alcohols, aluminum, chromium, titanium, zirconium, an acyl chloride, bis-diazobenzidine, phenol-2,4-disulfonyl chloride, 1,5-difluoro-2,4-dinitrobenzene, urea, 3,6-bis(mercurimethyl)-dioxane urea, dimethyl adipimidate and N,N'-ethylene-bis-iodacetamide; and
   (4) a biodegradable polymeric matrix comprising a cross-linked, water-insoluble protein, wherein said matrix formed upon the cross-linking of a water-soluble protein, and wherein said cross-linked, water-insoluble, protein is present at a concentration sufficient to provide said sustained-release composition with structural stability after being cross-linked, but not at so great a concentration as to render said sustained-release composition (i) incapable of biodegradation or (ii) incapable of permitting the release of said active agent.

3. A method for the administration of an active agent, wherein said method comprises the administration of a liquid precursor composition, wherein said liquid precursor composition solidifies to form a biodegradable sustained-release composition after said administration, said liquid precursor composition comprising:
   (1) a plasticizing agent, wherein said plasticizing agent is selected from the group consisting of a phthalate ester, a phosphate ester, a glycol derivative, a hydrocarbon, an oil, and a fatty acid;
   (2) said active agent, wherein said active agent is present in an amount sufficient to impart a desired therapeutic, agricultural, or catalytic property to said sustained-release composition;
   (3) a cross-linking agent, wherein said cross-linking agent is selected from the group consisting of aldehydes, alcohols, aluminum, chromium, titanium, zirconium, an acyl chloride, bis-diazobenzidine, phenol-2,4-disulfonyl chloride, 1,5-difluoro-2,4-dinitrobenzene, urea, 3,6-bis(mercurimethyl)-dioxane urea, dimethyl adipimidate and N,N'-ethylene-bis-iodacetamide; and (4) a water-soluble protein which is capable of being cross-linked into a water-insoluble, biodegradable polymeric matrix, wherein said water-soluble protein is present at a concentration sufficient to provide said sustained-release composition with structural stability after being cross-linked, but not at so great a concentration as to render said sustained-release composition (i) incapable of biodegradation or (ii) incapable of permitting the release of said active agent.

4. The composition of claim 2, wherein said cross-linking agent is present in said sustained-release composition in an amount sufficient to render said water soluble protein insoluble but not in an amount which prevents the release of said active agent from said sustained-release composition.

5. The composition of claim 1 or 2 wherein said cross-linking agent is present in said sustained-release composition in an amount of from about 0.01% to about 26%.

6. The composition of claim 1 or 2 wherein said cross-linking agent is an aldehyde selected from the group consisting of formaldehyde and glutaraldehyde.

7. The composition of claim 6 wherein said cross-linking agent is glutaraldehyde.

8. The composition of claim 1 or 2 wherein said cross-linked protein is cross-linked by incubation in the presence of cross-linking means, said means being selected from the group consisting of: heat, pressure, radiation, and the vapors of a cross-linking agent.

9. The composition of claim 8 wherein said cross-linked protein is cross-linked to an extent sufficient to render said water soluble protein insoluble but not to an extent which prevents the release of the active agent from said sustained-release composition.

10. A method for the administration of an active agent, wherein said method comprises the administration of a biodegradable sustained-release composition, said sustained-release composition comprising:
 (1) a plasticizing agent, wherein said plasticizing agent is selected from the group consisting of a phthalate ester, a phosphate ester, a glycol derivative, a hydrocarbon, an oil, and a fatty acid;
 (2) said active agent, wherein said active agent is present in an amount sufficient to impart a desired therapeutic, agricultural or catalytic property to said sustained-release composition;
 (3) a cross-linking agent, wherein said cross-linking agent is selected from the group consisting of aldehydes, alcohols, aluminum, chromium, titanium, zirconium, an acyl chloride, bis-diazobenzidine, phenol-2,4-disulfonyl chloride, 1,5-difluoro-2,4-dinitrobenzene, urea, 3,6-bis(mercurimethyl)-dioxane urea, dimethyl adipimidate and N,N'-ethylene-bis-iodacetamide; and
 (4) a biodegradable polymeric matrix comprising a cross-linked, water-insoluble protein, wherein said matrix formed upon the cross-linking of a water-soluble protein, and wherein said cross-linked, water-insoluble protein is present at a concentration sufficient to provide said sustained-release composition with structural stability after being cross-linked, but not at so great a concentration as to render said sustained-release composition (i) incapable of biodegradation or (ii) incapable of permitting the release of said active agent.

11. The composition of any one of claims 1 or 2 wherein said protein is selected from the group consisting of: gelatin, collagen, albumin, an enzyme, and fibrinogen.

12. The composition of claim 11 wherein said protein is gelatin.

13. The composition of claim 12 wherein said gelatin is hydrolyzed gelatin.

14. The composition of any one of claims 1 or 2 wherein said protein is present in said sustained release composition at a concentration of from about 14% to about 93%.

15. The composition of any one of claims 1 or 2 wherein said plasticizing agent is present in an amount sufficient to effect brittleness but not at so great a concentration as to prevent the release of the active agent.

16. The composition of claim 1 or 2 wherein said plasticizing agent is a glycol derivative.

17. The composition of claim 16 wherein said glycol derivative is selected from the group consisting of: glycerin and sorbitol.

18. The composition of claim 17 wherein said glycol derivative is glycerin.

19. The composition of any one of claims 1 or 2 wherein said plasticizing agent is in said sustained-release composition present at a concentration of from about 0.01% to about 52%.

20. The composition of any one of claims 1 or 2 wherein said active agent is a pharmacological agent.

21. The composition of claim 20 wherein said pharmacological agent is selected from the group consisting of: an analgesic, an anti-arrthymic drug, an anti-bacterial agent, an antibiotic, an antiviral agent, an anti-convulsant agent, an anti-fungal agent, an anti-pyretic agent, an anti-inflammatory agent, an anti-tumor agent, an anti-ulcer drug, a cardiovascular drug, a diuretic, a hormone, a hypoglycemic drug, a hypotensive drug, an ophthalmocological agent, a sedative, a hypnotic, and a tranquilizer.

22. The composition of claim 21 wherein said pharmacological agent is an antibacterial agent.

23. The composition of claim 22 wherein said antibacterial agent is selected from the group consisting of penicillin, cephalosporin, tetracycline, oxytetracycline, chlortetracycline, metronidazole, chloramphenicol, streptomycin, neomycin, a sulfonamide, a phenolic compound, a mercurial, a quarternary ammonium compound, and chlorhexidine.

24. The composition of claim 23 wherein said antibacterial agent is chlorhexidine.

25. The composition of claim 20 wherein said composition contains more than one pharmacological agent, said agent being selected from the group consisting of: an analgesic, an anti-arrthymic drug, an anti-bacterial agent, an antibiotic, an antiviral agent, an anti-convulsant agent, an anti-fungal agent, an anti-pyretic agent, an anti-inflammatory agent, an anti-tumor agent, an anti-ulcer drug, a cardiovascular drug, a diuretic, a hormone, a hypoglycemic drug, a hypotensive drug, an ophthalmocological agent, a sedative, a hypnotic, and a tranquilizer.

26. The composition of claim 25 wherein all of said pharmacological agents are selected from the same group of therapeutic agents, and wherein said group of therapeutic agents is selected from the group consisting of: an analgesic, an anti-arrthymic drug, an anti-bacterial agent, an antibiotic, an antiviral agent, an anti-convulsant agent, an anti-fungal agent, an anti-pyretic agent, an anti-inflammatory agent, an anti-tumor agent, an anti-ulcer drug, a cardiovascular drug, a diuretic, a hormone, a hypoglycemic drug, a hypotensive drug, an ophthalmocological agent, a sedative, a hypnotic, and a tranquilizer.

27. The composition of claim 20 wherein said sustained-release composition is substantially a two-dimensional film.

28. The composition of claim 27 wherein said film is from about 3 to about 10 mm in length, and from about 1 to about 5 mm in width, and from about 0.01 to 0.5 mm in depth.

29. A composition of claim 20 wherein said pharmacological agent and said protein are present in said sustained-release composition at a relative weight ratio which ranges from about 0.01:7 to about 3:1.

30. The composition of claim 20 wherein said plasticizing agent and said protein are present in said sustained-release composition at a relative weight ratio which ranges from about 0.01:7 to about 4:7.

31. The composition of claim 20 wherein said sustained-release composition has a flexibility which ranges from about 0.1 kg/mm$^2$ to about 50 kg/mm$^2$.

32. The method of any one of claims 3 or 10 wherein said composition is administered to said patient by means selected from the group consisting of: intra-nasal means, intra-ocular means, intra-aural means, subcutaneous means, transdermal means, topical application, and parenteral means.

33. The method of any one of claim 3 or 10 wherein said composition is administered as an implant selected from the group consisting of: a gingival crevice implant; a vaginal implant; and a testicular implant.

34. The method of claim 33 wherein said composition is administered as a gingival crevice implant.

35. A method for the treatment of a condition wherein said method comprises providing to a patient in need of such treatment the composition of any one of claims 1 or 2, wherein said composition contains a pharmacological agent capable of providing said treatment and wherein said pharmacological agent is present in an amount sufficient to impart therapeutic effect to said sustained-release composition.

36. The method of claim 35 wherein said composition is provided to said patient as an implant into a periodontal pocket of said patient.

37. The method of claim 36 wherein said pharmacological agent of said pharmaceutical composition is an antibacterial agent.

38. The method of claim 37 wherein said condition is periodontal disease, and wherein said antibacterial agent is effective in the treatment of said periodontal disease.

39. The method of claim 35 wherein said condition is pericoronitis.

40. The method of claim 35 wherein said treatment is an adjunct to endodontic treatment.

41. The method of claim 35 wherein said treatment is an adjunct to a tooth implantation procedure.

42. The method of claim 35 wherein said treatment is an adjunct to an epiectomy.

* * * * *

UNITED STATES PATENT AND TRADEMARK OFFICE
CERTIFICATE OF CORRECTION

PATENT : 5,023,082
DATED : June 11, 1991
INVENTOR(S) : FRIEDMAN et al.

It is certified that error appears in the above-identified patent and that said Letters Patent is hereby corrected as shown below:

On the title page, in the inventorship, item [75], between "Soskolne," and "all", insert ---Michael Sela--.

Column 7, line 52, delete "carbohydratehydrolizing" and insert therein --carbohydrate hydrolizing--.

Column 9, line 49, delete "Will" and insert therein --will--.

Column 16, line 23, delete "Were" and insert therein --were--.

Column 21, line 1, delete "Were" and insert therein --were--.

Column 23, Claim 4, line 11, between "claim" and "2", insert --1 or--.

Column 26, Claim 37, line 17, delete "pharmaceutical".

Signed and Sealed this

Third Day of January, 1995

Attest:

BRUCE LEHMAN

Attesting Officer

Commissioner of Patents and Trademarks